United States Patent [19]

Kawasaki et al.

[11] 4,407,799
[45] Oct. 4, 1983

[54] 2-SUBSTITUTED-PHENYL-1,3-PERHYDRO-THIAZINE-4-ONE

[75] Inventors: Takao Kawasaki, Sayama; Daisaku Immaru, Tama; Yoshiaki Osaka, Nagareyama; Tadashi Tsuchiya, Matsudo; Saichi Ono, Tokyo, all of Japan

[73] Assignee: Kureha Kagaku Kogyo Kabushiki Kaisha, Tokyo, Japan

[21] Appl. No.: 309,187

[22] Filed: Oct. 7, 1981

[30] Foreign Application Priority Data

Oct. 9, 1980 [JP] Japan ................................. 55-141240

[51] Int. Cl.³ .................... C07D 279/06; A61K 31/54
[52] U.S. Cl. ...................................... 424/246; 544/54
[58] Field of Search .......................... 544/54; 424/246

[56] References Cited

U.S. PATENT DOCUMENTS 3,082,209 3/1963 Surrey .................................. 544/54

FOREIGN PATENT DOCUMENTS 624416 7/1961 Canada ................................... 544/54
2055816 3/1981 United Kingdom .

OTHER PUBLICATIONS

Chemical Abstracts, vol. 84, 1976, p. 472, 164801x.
Chemical Abstracts, vol. 85, 1976, p. 457, 5655g.

*Primary Examiner*—John M. Ford
*Attorney, Agent, or Firm*—Wegner & Bretschneider

[57] ABSTRACT

Compounds of 2-substituted-phenyl-1,3-perhydrothiazine-4-one having the formula (I)

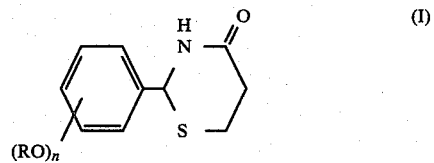

wherein R represents a lower alkyl group of 1 to 3 carbon atoms and n denotes an integer of 1 to 3 possess anti-peptic ulcer activity.

4 Claims, No Drawings

2-SUBSTITUTED-PHENYL-1,3-PERHYDROTHIAZINE-4-ONE

BACKGROUND AND SUMMARY OF THE INVENTION

The present invention concerns novel compounds, their preparation and their use as anti-peptic ulcer medicine. More particularly, the present invention concerns novel compounds of 2-substituted-phenyl-1,3-perhydrothiazine-4-one which are useful as anti-peptic ulcer medicines.

Originally, the peptic ulcer is the collapsed weakened parts of the gastric or enteric mucosa by the action of aggressive factors such as hydrochloric acid and pepsin in the gastric juice. The mild cases of peptic ulcer are curable after 3 to 4 month of hospitalization and treatment, however, the serious cases are accompanied by hemorrhage and perforation of the organ and become chronic.

As an etiological cause of peptic ulcer, the abnormalities in the autonomic nerve system and in the mucosal blood flow due to physical and/or mental stress has been considered, however, it is practically impossible to interpret the etiology of peptic ulcer unitarily because the viscera themselves are subjected to complicated control by the nerves and hormones.

Hitherto, as an anti-peptic ulcer medicine, sodium hydrogen carbonate, alminum salts and magnesium salts have been used for a long time in the meaning of neutralizing the above-mentioned acid as the aggressive factor. However, these medicines only temporarily neutralize the acid to alleviate the pain and do not accelerate the substantial cure of the ulcer.

Recently, many kinds of anti-ulcer medicines have been developed based on the presumable causes of ulcer, including the medicines suppressing autonomic nerve, that is, so-called anti-cholinergic agents, the agents repairing the damaged tissues and the agents improving the blood flow. However, the present situation is that none of them can be said to be satisfactory in view of their effectiveness or their side effects.

For instance, carbenoxolone which has been commercialized as an anti-peptic ulcer medicine has been broadly used because of its excellent accelerating effect on the ulcer-curing, however, it has an aldosterone-like side effects to cause hypertension and weakening of muscular function when taking continuously. In addition, the above-mentioned anti-cholinergic agent shows severe side effects such as mydriasis and thirst due to the blocking of the parasympathetic nerve, and it has been reported their effects of accelerating the ulcer-curing is low.

Since it generally takes a long time period for curing the peptic ulcer, the period of administration of an anti-peptic ulcer medicine extends to 100 to 150 days on the average. And accordingly, it is required that the anti-peptic ulcer medicine is highly safe as well as highly effective in ulcer-curing.

An object of the present invention provides an anti-peptic ulcer medicine excellent in anti-peptic ulcer action and pharmacologically safe.

Another object of the present invention provides a compound useful as an anti-peptic ulcer medicine.

DETAILED EXPLANATION OF THE INVENTION

The novel compounds according to the present invention are 2-substituted-phenyl-1,3-perhydrothiazine-4-one represented by the following formula:

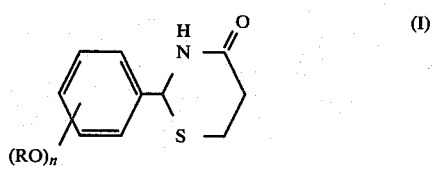

wherein R is a lower alkyl group of 1 to 3 carbon atoms, and n is an integer of 1 to 3.

2-Substituted-phenyl-1,3-perhydrothiazine-4-one represented by the above-mentioned formula (I) have excellent anti-peptic ulcer action and are pharmacologically safe compounds.

2-Substituted-phenyl-1,3-perhydrothiazine-4-one according to the present invention (hereinafter referred to as the present compounds) include the following compounds:

2-(3,4,5-trimethoxyphenyl)-1,3-perhydrothiazine-4-one,
2-(2,3,4-trimethoxyphenyl)-1,3-perhydrothiazine-4-one,
2-(2,3-dimethoxyphenyl)-1,3-perhydrothiazine-4-one,
2-(2,4-dimethoxyphenyl)-1,3-perhydrothiazine-4-one,
2-(2,5-dimethoxyphenyl)-1,3-perhydrothiazine-4-one,
2-(2,6-dimethoxyphenyl)-1,3-perhydrothiazine-4-one,
2-(3,4-dimethoxyphenyl)-1,3-perhydrothiazine-4-one,
2-(3,5-dimethoxyphenyl)-1,3-perhydrothiazine-4-one,
2-(2-methoxyphenyl)-1,3-perhydrothiazine-4-one,
2-(3-methoxyphenyl)-1,3-perhydrothiazine-4-one and
2-(4-methoxyphenyl)-1,3-perhydrothiazine-4-one.

The melting points, appearances and elementary analytical compositions of the present compounds are shown in Table 1.

TABLE 1

| Compound number | Name of compound | Structural formula | Melting point (°C.) | Appearance | C | H | N | S |
|---|---|---|---|---|---|---|---|---|
| 1 | 2-(3,4,5-trimethoxyphenyl)-1,3-perhydrothiazine-4-one | | 181–182 | colourless acicular | 55.09 (55.11) | 6.07 (6.05) | 4.92 (4.94) | 11.29 (11.32) |
| 2 | 2-(3,4-dimethoxyphenyl)-1,3-perhydrothiazine-4-one | | 166–167 | colourless minute acicular | 56.92 (56.90) | 5.96 (5.97) | 5.53 (5.53) | 12.69 (12.66) |

TABLE 1-continued

| Compound number | Name of compound | Structural formula | Melting point (°C.) | Appearance | Elementary analytical composition (%) | | | |
|---|---|---|---|---|---|---|---|---|
| | | | | | C | H | N | S |
| 3 | 2-(2-methoxyphenyl)-1,3-perhydrothiazine-4-one | | 201.5–203 | colourless prism | 59.14 (59.17) | 5.90 (5.87) | 6.25 (6.27) | 14.39 (14.36) |
| 4 | 2-(4-methoxyphenyl)-1,3-perhydrothiazine-4-one | | 185.5–186.5 | colourless acicular | 59.19 (59.17) | 5.86 (5.87) | 6.26 (6.27) | 14.37 (14.36) |

Note:
The parenthesized values in Elementary Analytical Composition represent the theoretical values based on the molecular formula of each compound.

The present compound may be produced by either of the following two methods (1) and (2):

(1) A process which comprises reacting an aldehyde represented by the formula (II):

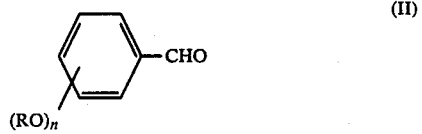

wherein R represents a lower alkyl group of 1 to 3 carbon atoms and n is an integer of 1 to 3, with 3-mercaptopropionic acid or an ester thereof and an ammonium compound in an inert solvent such as benzene, toluene and xylene. Preferably an equimolar or a slight excess of the 3-mercaptopropionic acid or ester thereof is used. The ammonium compound, preferably ammonium carbonate, is used in an amount of a slight excess as ammonia. The reaction can be carried out at a temperature of 50° to 150° C., usually at the boiling point of the solvent for 1 to 10 hours.

The method (1) can be summarized as follows:

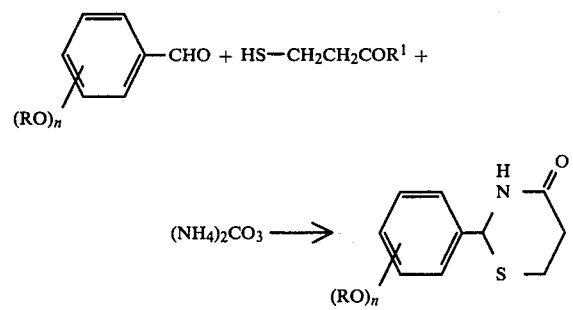

wherein R represents a lower alkyl group with 1 to 3 carbon atoms, R[1] represents a hydroxyl group or an alkoxy group with 1 to 2 carbon atoms, and n denotes an integer of 1 to 3.

(2) A process which comprises reacting an aldehyde represented by the formula (II) with 3-mercaptopropionic acidamide in an inert solvent such as benzene, toluene and xylene. Preferably an equimolar or slight excess of 3-mercaptopropionic acidamide is used. The reaction can be carried out at a temperature of 50° to 150° C., usually at the boiling point of the solvent, for 1 to 3 hours.

No matter which method may be adopted, on cooling the reaction mixture after the reaction is over, the object product separates out as crystals, and accordingly, the crystals are collected by filtration and using a solvent ordinarily used for recrystallization such as benzene, methanol or ethanol, they are purified by recrystallization.

In the next place, the pharmacological and toxicological properties of the present compounds are explained.

The important problem in the development of anti-peptic ulcer medicine is the screening system thereof. Hitherto, the evaluation of anti-ulcer medicines has been frequently carried out based on their prophylactic effect against the acute ulcer such as ulcer due to pyloric ligation, aspirin or indomethacin. However, to what extent the result of evaluation by these ulcer models reflect the curing effect on human ulcer has not been fully elucidated.

The inventors of the present invention, taking into account of these situations, added to the above-mentioned method of evaluation the effect of accelerating the cure of the peptic ulcer by orally administering the present compound and a commercialized anti-peptic ulcer medicine, respectively to rats to which duodenal peptic ulcer due to acetic acid (refer to Okabe, 1971) considered to be most closely resembling to human peptic ulcer has been artificially formed.

Anti-peptic ulcer effect of the present compound (1) Effect on peptic ulcer due to pyloric ligation Six groups (10 animals per group) of male rats weighing 180 to 200 g were subjected to ligation of their pyloruses under ether-anesthesia after fasting for 48 hours according to the method of Shay et al. (refer to Gastroenterology, 5, page 43 (1945)).

Just after subjecting to ligation, each of the present compound suspended in an aqueous physiological saline solution was intraperitoneally administered to each rat, the control being injected with an aqueous physiological saline solution. Then, after 15 hours of fasting without taking water, the rats were sacrificed with ether and their stomachs were removed to examine under a microscope for anatomy. The length and width of the thus-formed ulcer in the stomach were determined and expressed by the product (mm$^2$), and the total sum of the products was represented as the ulcer coefficient. The results are shown in Table 2.

TABLE 2

| Compound number | Dose rate (mg/kg) | Ulcer coefficient (mm$^2$) | Rate of suppression[1] |
|---|---|---|---|
| 1 | 100 | 9.3 | 74.9 |
| 2 | 100 | 1.9 | 94.3 |
| 3 | 100 | 2.4 | 93.5 |
| 4 | 100 | 2.0 | 94.5 |
| Positive control[2] | 100 | 32.5 | 12.2 |
| Control | — | 37.0 | 0 |

Notes
[1]Rate of suppression of ulcer = 
$$\frac{\text{Ulcer coefficient (control)} - \text{Ulcer coefficient (treated group)}}{\text{Ulcer coefficient (control)}} \times 100$$
[2]Positive control: Gefarnate = 3,7-dimethyl-2,6-octadienyl-5,9,13-trimethyl-4,8,12-tetradecatrienoate (2) Effect on peptic ulcer due to acetic acid Following the method of Okabe et al (refer to Amer. J. Dig. Dis., 16, (1977)), 6 groups (15 animals per group) of male rats weighing 240 to 260 g were subjected to laparotomy under ether anesthesia in which a metal circular frame was placed on the serosa at a distance of 5 to 7 mm from the duodenal pylorus, 0.06 ml of glacial acetic acid was poured into the frame. After 30 seconds, the liquid containing the acetic acid was removed and then the frame was removed. The test compound suspended in an aqueous 0.5% solution of carboxymethylcellulose was orally administered to the rat 3 times a day from the third day of the operation for consecutive 10 days. To the control group, only the solution of carboxymethylcellulose was administered. After the administration was over, the rats were sacrificed with ether, and their duodenum was removed to observe under a microscope for anatomy. The length and width of the thus-formed ulcer were measured and their product (expressed with mm$^2$) was recorded as the ulcer coefficient. The results are shown in Table 3.

TABLE 3

| Compound number | Dose rate (mg/kg) | Ulcer coefficient (mm$^2$) | Rate of suppression of ulcer (%) |
|---|---|---|---|
| 1 | 100 | 2.5 | 67.1 |
| 2 | 100 | 2.0 | 73.6 |
| 3 | 100 | 1.5 | 80.2 |
| 4 | 100 | 1.3 | 82.8 |
| Positive control[1] | 100 | 6.1 | 20.0 |
| Control | — | 7.6 | 0 |

Note:
[1]Positive control: gefarnate (refer to the footnote of Table 2)

By the way, the above-mentioned experimental model has been highly evaluated internationally because the thus-formed ulcer is scarcely curable in nature and the histopathological change of the ulcer lesion closely resembles to that of human chronic ulcer as compared to the method of cautery-ulcer (refer to Skoryna, 1958) and the method of crumping-cortisone (refer to Umehara, 1965).

(3) On the evaluation by the hitherto broadly utilized effective methods for screening anti-peptic ulcer medicines such as those of stress-ulcer, aspirin-ulcer and indomethacin-ulcer, the present compounds showed superior effects to the effects of commercialized anti-peptic ulcer medicines.

Toxicological properties of the present compound (1) Acute toxicity test

Experimental animal:
Female ICR-mice of body weight of 20 to 24 g, 5 weeks after birth were used.

Method of rearing:
Eight animal per group were kept in a transparent polycage at room temperature of 23°±1° C., and RH of 60 to 70%.

Administration of the present compound:
After minutely pulverizing each one of the present compounds, the pulverized compound was suspended in an aqueous 5% sodium carboxymethylcellulose solution containing 20% of Tween-80. The aqueous suspension was forcibly orally administered by a metal stomach tube, the dose rate having been adjusted by changing the concentration of the present compound in the aqueous suspension.

General symptoms due to the present compound:
In cases of administering at higher dose rate, the movement of the rats became inactive, however, after 2 to 3 hours, they became normal. In some mortal cases, the rat's spontaneous movement was lowered with the reduction of general tension and the rats died as they were.

Calculation of LD$_{50}$:
The rats' mortality was observed for a week after the administration, and LD$_{50}$ was calculated from the mortality by the Litchfield-Wilcoxon's formula. The results are shown in Table 4.

TABLE 4

| Compound number | LD$_{50}$(p.o.) (mg/kg) |
|---|---|
| 1 | 5400 |
| 2 | more than 8000 |
| 3 | more than 8000 |
| 4 | more than 8000 |

In addition, according to the results of acute toxicity test using rats and mice as experimental animals, LD$_{50}$ i.v. was larger than 1.5 g/kg.

(2) Sub-acute toxicity test

Experimental animal:
Both sexes of Sprague-Dowley rats of 110 to 150 g of body weight after 5 months of their birth were used.

Method of rearing:
Each five males and five females were respectively kept in a metal wire-net cage at room temperature of 22° to 24° C. and RH of 60 to 70% for 3 months, each experimental group consisting of 10 males or 10 females.

Administration of the present compound:
Compound No. 2 of the present compounds, 2-(3,4-dimethoxyphenyl)-1,3-perhydrothiazine-4-one, was minutely pulverized and mixed with the powdery diet for rat at a concentration of 0.4% by weight. The thus prepared diet was taken ad lib. The mean intake of the present compound was 400 mg/kg/day.

Examination:
The diet intake and the body weight of each rat were measured every other day and once a week, respectively. The urinalysis for glucose, protein, pH, and occult blood was carried out once a month. Blood sample was examined after ending the rearing, and after sacrificing all the animals, they were autopsied to examine the presence of abnormalities. Their organs were fixed with formaldehyde and imbedded in paraffin to prepare sliced specimens of tissues stained with hematoxylineosine for microscopic observation.

Results:
(a) Diet intake was normal without significant difference between experimental groups and control group.
(b) Body weight gain was normal without significant difference between experimental groups and control group.
(c) Mortality, (d) urinalysis, (c) hematological examination, and (f) findings on autopsy and histological examination were all normal without any significant difference between experimental groups and control group.

Further, in the sub-acute toxicity test using mice as experimental animals, abnormal findings attributable to the present compound could never be obtained.

As is seen above, the present compound is highly safe for administration and accordingly, it can be used as an anti-peptic ulcer medicine in human cases.

In addition to its excellent pharmacological effects and toxicological properties, every compound of the present invention is colourless and crystalline, and almost of them are tasteless or are only slightly bitter. Furthermore, since they are extremely stable without any change after storing at room temperature in an open state, their adaptability as an anti-peptic ulcer medicine can be said remarkably high.

A pharmaceutical composition according to the present invention is useful for treatment of peptic ulcer, and comprises a therapeutically effective amount of the present compound together with a pharmaceutically acceptable carrier. The pharmaceutical composition is in unit dosage form, e.g. as tablets, sugar-coated tablets, pills, capsules, powders, granules, troches, liquids, suppositories, injections, etc.

As the carrier, lactose, sucrose, sorbitol, mannitol, potato-starch, corn-starch, amylopectin, various kinds of starch, derivatives of cellulose (for instance carboxymethylcellulose and methylcellulose), gelatin, magnesium stearate, calcium stearate, polyvinyl alcohol, polyethylene glycol waxes, gum arabic, talk, titanium dioxide, vegetable oil such as olive oil, peanut oil and sesame oil, paraffin oil, neutral fatty bases, ethanol, aqueous physiological saline solutions, sterilized water, glycerol, colouring agents, flavorings, thickening agents, stabilizers, isotonic agents and buffering agent can be exemplified.

The content of the one of the present compounds in the above-mentioned pharmaceutical composition is 0.1 to 90% by weight, preferably 1 to 60% by weight of the preparation.

The clinical daily dose of the present compound is 60 to 6000 mg/60 kg of body weight, preferably, 600 to 3000 mg/60 kg body weight. The route of administration may oral or injectional, and it is preferably administered orally in the case of long term administration.

The followings are the more detailed explanation of the present invention while referring to examples, however, it should be understood that the scope of the present invention is never restricted to Examples shown as follows:

SYNTHETIC EXAMPLES OF THE PRESENT COMPOUNDS

EXAMPLE 1

Synthesis of 2-(3,4,5-trimethoxyphenyl)-1,3-perhydrothiazine-4-one

A mixture of 19.6 g of 3,4,5-trimethoxybenzaldehyde, 10.6 g of 3-mercaptopropionic acid and 6 g of ammonium carbonate in 250 ml of benzene was refluxed for 5 hours at 80° C. in a flask provided with a Dean-Stark apparatus and the thus distilled water was removed. The crystals which separated out from the reaction mixture after reaction was over and on cooling the reaction mixture, were collected by filtration and recrystallized from benzene to give 21.8 g of colourless aciculates melting at 181° to 182° C. in a yield of 77%.

EXAMPLE 2

Synthesis of 2-(3,4-dimethoxyphenyl)-1,3-perhydrothiazine-4-one

A mixture of 16.6 g of 2,4-dimethoxybenzaldehyde, 10.6 g of 3-mercaptopropionic acid and 6 g of ammonium carbonate in 250 ml of benzene was refluxed for 3 hours in a reaction vessel provided with a Dean-Stark apparatus at 80° C. while removing the distilled water. The crystals which separated out after cooling the reaction mixture were collected by filtration and recrystallized from hot benzene to obtain the object, colourless minute acicular crystals melting at 166° to 167° C. in an amount of 22 g corresponding to a yield of 87%.

EXAMPLE 3

Synthesis of 2-(2-methoxyphenyl)-1,3-perhydrothiazine-4-one

A mixture of 13.6 g of o-anisaldehyde, 10.6 g of 3-mercaptopropionic acid and 6 g of ammonium carbonate in 250 ml of toluene was refluxed at 110° C. for 2 hours in a flask provided with a Dean-Stark apparatus while removing the distilled water. The crystals which separated out after leaving the reaction mixture for a night were collected by filtering and recrystallized from hot dimethylformamide to obtain the object, colourless prisms melting at 201.5° to 203° C. in an amount of 18.7 g corresponding to a yield of 84%.

EXAMPLE 4

Synthesis of 2-(4-methoxyphenyl)-1,3-perhydrothiazine-4-one

A mixture of 13.6 g of p-anisaldehyde and 10.5 g of 3-mercaptopropionic acid amide in 150 ml of benzene was heated at 80° C. for 2 hours. The crystals which separated out after leaving the reaction mixture for a night were collected by filtration and recrystallized from hot benzene to obtain colourless minute aciculates melting at 185.5° to 186.5° C. in an amount of 21 g corresponding to a yield of 94%.

MANUFACTURE OF THE PHARMACEUTICAL PREPARATIONS

EXAMPLE 5

Manufacture of the granular preparation for oral administration

Two hundred grams of 2-(3,4-dimethoxyphenyl)-1,3-perhydrothiazine-4-one was minutely pulverized and 800 g of corn-starch was admixed with the pulverized compound. After stirring the mixture well, 80 ml of an aqueous solution containing 3 g of sodium carboxymethylcellulose dissolved therein was added to the mixture, and after kneading the whole mixture, it was subjected to an extruding pelletizer to be granular shape. The shaped mixture was dried at a temperature of 60° to 80° C. and screened to obtain the granular preparation for oral administration.

What is claimed is:

1. A process for preparing a compound of 2-substituted phenyl-1-1, 3-perhydrothiazine-4-one represented by the formula

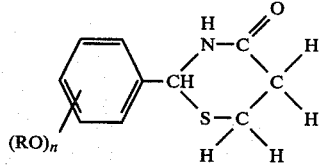

wherein R represents a lower alkyl group of 1 to 3 carbon atoms and n denotes in integer of 1 to 3, which comprises reacting an aldehyde represented by the formula

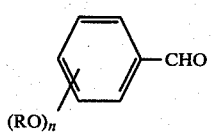

wherein R and n are as defined above, with 3-mercaptopropionic acid amide in an inert solvent.

2. A process according to claim 1, wherein the reaction is carried out at a temperature of 50° to 150° C.

3. A pharmaceutical anti-ulcer composition in a dosage unit form, which comprises a dosage effective for treatment of peptic ulcer of a 2-substituted phenyl-1,3-perhydrothiazine-4-one represented by the formula

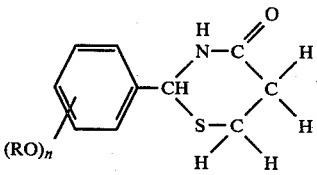

wherein R represents a lower alkyl group of 1 to 3 carbon atoms and n denotes an integer of 1 to 3, and a pharmaceutically acceptable carrier.

4. A method for treatment of peptic ulcer which comprises administering to an animal suffering from peptic ulcer an amount effective for treatment of peptic ulcer of a 2-substituted phenyl-1,3-perhydrothiazine-4-one represented by the formula

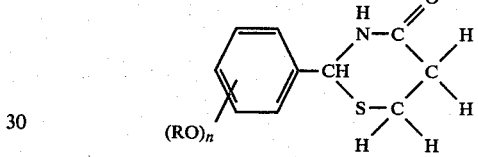

wherein R represents a lower alkyl group of 1 to 3 carbon atoms and n denotes an integer of 1 to 3.

* * * * *